United States Patent
Shimasaki

(10) Patent No.: US 10,099,189 B2
(45) Date of Patent: Oct. 16, 2018

(54) PACKING FOR REACTION TUBE, REACTION TUBE, AND REACTION METHOD USING SAME

(71) Applicant: NIPPON SHOKUBAI CO., LTD., Osaka (JP)

(72) Inventor: Yuuji Shimasaki, Hyogo (JP)

(73) Assignee: NIPPON SHOKUBAI CO., LTD., Osaka (JP)

( * ) Notice: Subject to any disclaimer, the term of this patent is extended or adjusted under 35 U.S.C. 154(b) by 0 days.

(21) Appl. No.: 15/033,749

(22) PCT Filed: Oct. 30, 2014

(86) PCT No.: PCT/JP2014/078971
§ 371 (c)(1),
(2) Date: May 2, 2016

(87) PCT Pub. No.: WO2015/068640
PCT Pub. Date: May 14, 2015

(65) Prior Publication Data
US 2016/0279587 A1 Sep. 29, 2016

(30) Foreign Application Priority Data
Nov. 7, 2013 (JP) .................. 2013-231370

(51) Int. Cl.
*B01J 19/30* (2006.01)
*B01J 7/00* (2006.01)
(Continued)

(52) U.S. Cl.
CPC .................. *B01J 7/00* (2013.01); *B01J 8/067* (2013.01); *B01J 19/30* (2013.01); *C07C 37/58* (2013.01);
(Continued)

(58) Field of Classification Search
CPC ..... C07C 37/58; C07C 51/252; C07D 301/08; C07D 307/60; B01J 7/00; B01J 8/067;
(Continued)

(56) References Cited

U.S. PATENT DOCUMENTS

| 3,801,634 A | 4/1974 | Krabetz et al. |
| 4,837,360 A | 6/1989 | Kadowaki et al. |

(Continued)

FOREIGN PATENT DOCUMENTS

| JP | 53-30688 | 8/1978 |
| JP | 61-54229 | 3/1986 |

(Continued)

OTHER PUBLICATIONS

International Search Report dated Feb. 3, 2015 in International (PCT) Application No. PCT/JP2014/078971.
(Continued)

*Primary Examiner* — Taylor V Oh
(74) *Attorney, Agent, or Firm* — Wenderoth, Lind & Ponack, L.L.P.

(57) ABSTRACT

In a fixed-bed flow reaction using a multitubular heat exchange type reactor, an object of the present invention is to provide a novel packing for a reaction tube, which can control the reaction ratio in the vicinity of the reaction tube inlet, reduce the load unevenly placed on the catalyst in the reaction region, and distribute the load on the entire catalyst layer, a heat exchange type reactor, and a reaction method using the reaction tube. The packing for a reaction tube of the present invention is characterized in that the volume is continuously or step-by-step decreased from one end part or midway toward the other end part.

12 Claims, 5 Drawing Sheets

(51) Int. Cl.
*C07D 307/60* (2006.01)
*B01J 8/06* (2006.01)
*C07C 37/58* (2006.01)
*C07C 51/25* (2006.01)
*C07D 301/08* (2006.01)

(52) U.S. Cl.
CPC .......... *C07C 51/252* (2013.01); *C07D 301/08* (2013.01); *C07D 307/60* (2013.01); *B01J 2208/065* (2013.01); *B01J 2219/30223* (2013.01); *B01J 2219/30226* (2013.01); *B01J 2219/30253* (2013.01); *B01J 2219/30408* (2013.01); *B01J 2219/30416* (2013.01)

(58) Field of Classification Search
CPC .............. B01J 19/30; B01J 2219/30416; B01J 2219/30253; B01J 2219/30223; B01J 2219/30408; B01J 2219/30226
USPC .................................. 549/523; 422/310, 312
See application file for complete search history.

(56) References Cited

U.S. PATENT DOCUMENTS

| | | |
|---|---|---|
| 2006/0024222 A1 | 2/2006 | Dachs et al. |
| 2006/0041030 A1* | 2/2006 | Lehr ........................ B01J 8/065 518/702 |
| 2006/0054314 A1 | 3/2006 | Mauvezin et al. |
| 2007/0122322 A1 | 5/2007 | Te Raa et al. |
| 2009/0272673 A1 | 11/2009 | Gaemers |
| 2010/0278700 A1 | 11/2010 | Clawson et al. |

FOREIGN PATENT DOCUMENTS

| | | |
|---|---|---|
| JP | 62-1736 | 1/1987 |
| JP | 63-38331 | 7/1988 |
| JP | 4-126735 | 11/1992 |
| JP | 11-80052 | 3/1999 |
| JP | 2006-142299 | 6/2006 |
| JP | 2009-520094 | 5/2009 |
| JP | 2013-107873 | 6/2013 |
| WO | 2004/056463 | 7/2004 |
| WO | 2009/057463 | 5/2009 |

OTHER PUBLICATIONS

Notification of Reasons for Rejection dated Oct. 25, 2016 in corresponding Japanese Application No. 2015-546619, with English translation.
First Notification of Office Action dated Jan. 19, 2017 in corresponding Chinese Application No. 201480060400.X, with English translation.
Extended European Search Report dated Jun. 9, 2017 in corresponding European Application No. 14859584.6.
Chinese Office Action dated Jul. 26, 2017 in corresponding Chinese Patent Application No. 201480060400.X with English translation.

* cited by examiner

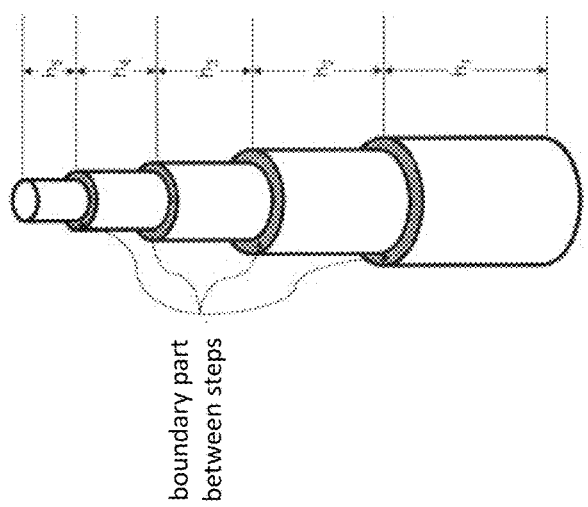
[Fig.3]
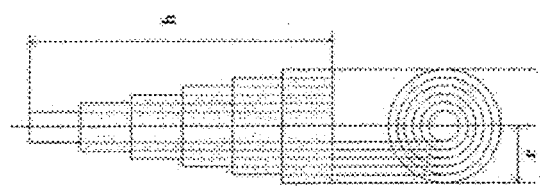
[Fig.2]
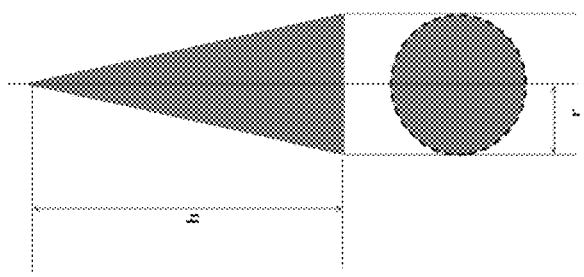
[Fig.1]

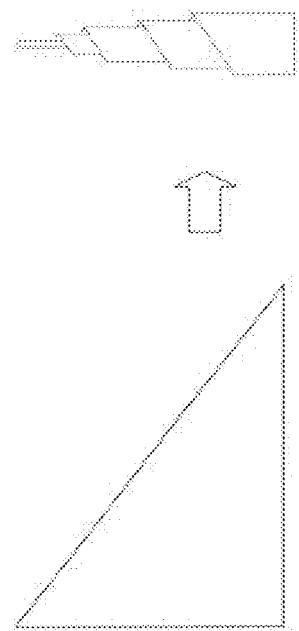
[Fig.5]
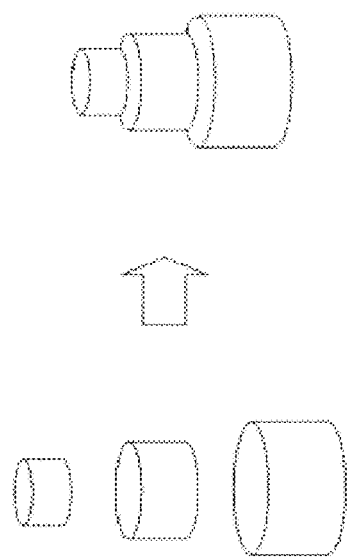
[Fig.4]

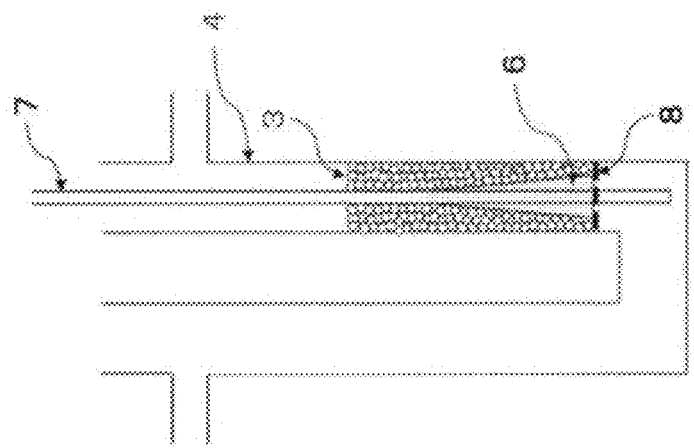
[Fig.7]
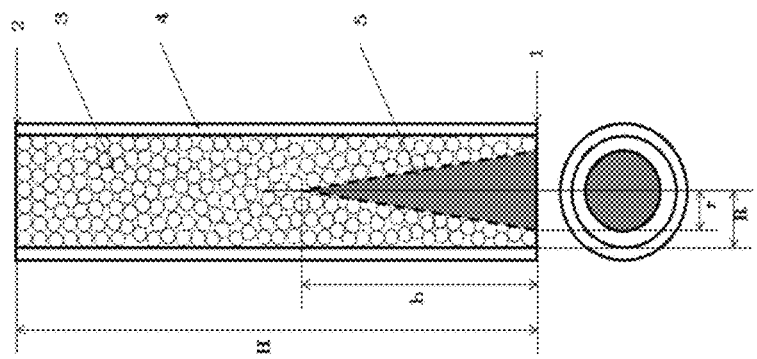
[Fig.6]

[Fig. 8]
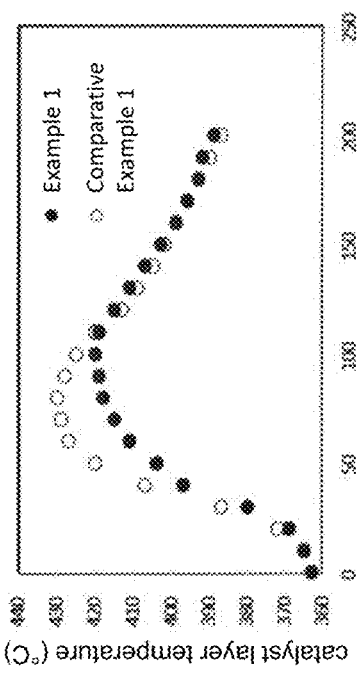
[Fig. 9]
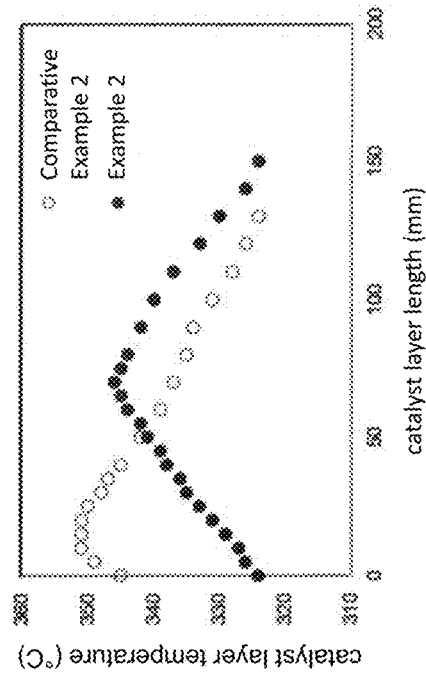
[Fig. 10]
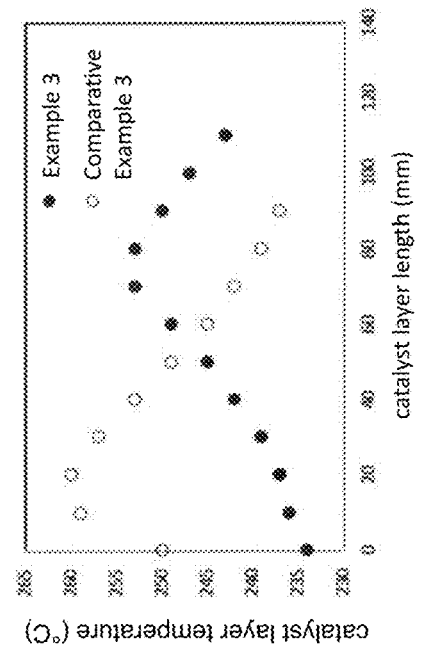

[Fig.12]
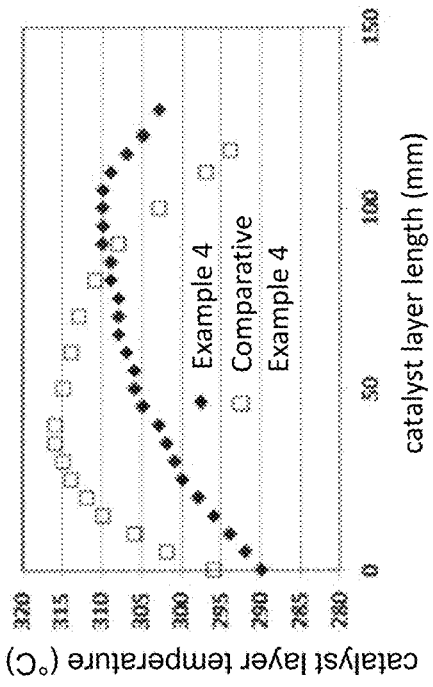
[Fig.13]
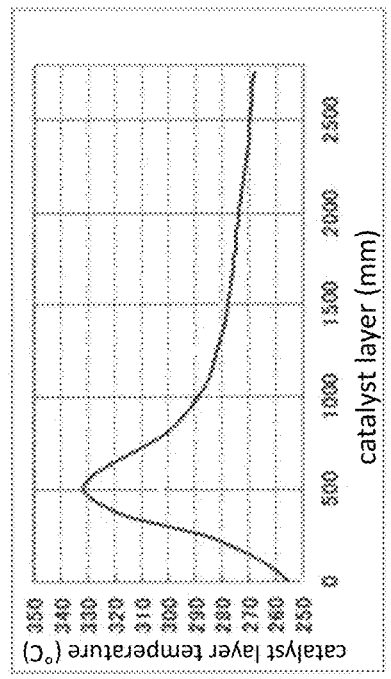
[Fig.11]
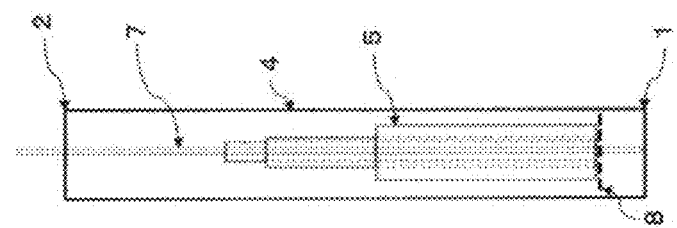

PACKING FOR REACTION TUBE, REACTION TUBE, AND REACTION METHOD USING SAME

TECHNICAL FIELD

The present invention relates to a packing for a reaction tube, a reaction tube, a heat exchange type reactor, and a reaction method using the reaction tube. More particularly, the present invention relates to a packing for a reaction tube, which can reduce a reaction ratio in the vicinity of a reaction tube inlet, suppress nonuniformity of a load on a catalyst in the vicinity of the reaction tube inlet, and prevent generation of a local high temperature part or a local low temperature part in an exothermic or endothermic catalytic reaction carried out using a heat exchange type reactor, a reaction tube, a heat exchange type reactor, and a reaction method using the reaction tube.

BACKGROUND ART

In the case where a fixed-bed flow reaction by continuously feed of a reaction raw material into a heterogeneous solid catalyst with endotherm or exotherm, a multitubular heat exchange type reactor is generally used.

Particularly, in the case of industrial execution of a vapor-phase oxidation that emits large amount of heat or a vapor-phase dehydration that absorbs large amount of heat, a multitubular heat exchange type reactor has been used. The vapor-phase oxidation that emits large amount of heat may include, for example, ethylene oxide production by oxidation of ethylene, acrolein and acrylic acid production by oxidation of propylene, methacrolein and methacrylic acid production by oxidation of isobutylene, and maleic anhydride production by oxidation of benzene. The vapor-phase dehydration that absorbs large amount of heat may include, for example, ethyleneimine production by dehydration of monoethanolamine, and N-vinyl-2-pyrrolidone production by dehydration of N-(2-hydroxyethyl)-2-pyrrolidone.

A multitubular heat exchange type reactor used industrially is equipped with several thousands to several tens of thousands of reaction tubes having an inner diameter of 20 to 50 mm and a length of 1 to 20 m and is filled with a solid catalyst, and is so designed as to remove or supply heat in a reaction by contacting a heat medium with these reaction tubes. In general, the heat medium of the multitubular heat exchange type reactor is so designed as to make the temperature uniform as much as possible in the entire region in which the reaction tubes have contact with the heat medium. Therefore, the load on the catalyst in the vicinity of the reaction tube inlet, where the reaction raw material concentration is high, is large to result in significant unevenness of deterioration of the catalyst from the reaction tube inlet to the outlet, and it may sometimes quicken the stage at which the reactor can no longer exhibit the desired performance.

For example, in the case of an exothermic reaction, heat removal from the vicinity of the reaction tube becomes insufficient, so that not only the catalyst layer temperature increases and side reactions increase, but also the catalyst may be damaged and runaway reaction may occur. In the case of an endothermic reaction, heat supply in the vicinity of the reaction tube inlet becomes insufficient, and the conversion may be reduced.

Many vapor-phase catalytic reactions carried out industrially include a step of regenerating a catalyst by periodically burning out carbonaceous materials accumulated on the catalyst. In such a case, removal of combustion heat in the vicinity of the reaction tube inlet in which a large amount of carbonaceous materials accumulated is sometimes insufficient, which may result in catalyst damages due to increase of the catalyst layer temperature. In general, it takes a long time to regenerate the catalyst since carbonaceous materials are burned gradually at a low oxygen concentration to avoid the temperature increase.

Methods known as a countermeasure against the problem caused in the catalyst layer in the vicinity of the reaction tube inlet are to reduce the reaction ratio in the vicinity of the reaction tube inlet by filling the vicinity of the reaction tube inlet with a diluted catalyst mixed with an inert material to the reaction or a catalyst with suppressed catalytic activity (Patent Document 1 and Patent Document 2). However, these methods are extremely complicated because the reaction tube inlet has to be uniformly filled with a catalyst or an inert material, and require a large quantity of labor and time. Further, these methods have a problem of increase of the pressure loss of the catalyst layer, and consequent increase of motive power for reaction gas supply.

Patent Document 3 and Patent Document 4 disclose methods for optimizing the reaction ratio in the vicinity of the reaction tube inlet by reducing the reaction tube inner diameter step-by-step from the reaction tube inlet to the outlet to control the temperature characteristics in the entire length of the reaction tubes. However, the cost of manufacturing the reaction tubes is high, and the reactor has a problem in mechanical strength at the connection part between reaction tubes having different diameters, and durability against thermal strain.

As a method for avoiding generation of hot spots, Patent Document 5 discloses a method for preventing local abnormally-high temperature part by installing a metal rod in the axial centers of reaction tubes. This method reduces the temperature gradient conventionally caused in the radius direction of reaction tubes, and is effective for suppressing temperature increase in the center parts of the tube axes. However, because the cross-sectional area of the catalyst layer gradually increases from the vicinity of the tip end of the metal rod, generation of a second local abnormally-high temperature part in the vicinity of the tip end is easily presumed.

Further, Patent Document 6 discloses a method for isolating a portion of a raw material gas from the catalyst by installing a hollow tube in the inside of reaction tubes. This method is effective for preventing generation of a local abnormally-high temperature part by flowing a raw material gas into the hollow tube and thus preventing the raw material gas from contacting the high temperature part. However, the method disclosed in Patent Document 6 divides the inside of the reaction tubes into two regions with different reaction ratios to make the catalyst load significantly uneven. For example, in Examples of Patent Document 6, two temperature peaks are observed.

PRIOR ART DOCUMENTS

Patent Documents

Patent Document 1: JP-A-syo-53-30688
Patent Document 2: JP-A-syo-63-38331
Patent Document 3: WO04/056463
Patent Document 4: JP-A-2013-107873
Patent Document 5: JP-A-hei-11-80052
Patent Document 6: WO09/057463

SUMMARY OF THE INVENTION

Problems to be Solved by the Invention

An object of the present invention is to solve the above-mentioned problems caused in the catalyst layer in the vicinity of the reaction tube inlet. That is, in a fixed-bed flow reaction using a multitubular heat exchange type reactor, the present invention provides a novel packing for a reaction tube, which can control the reaction ratio in the vicinity of the reaction tube inlet, reduce the load unevenly placed on the catalyst in the reaction region, and distribute the load on the entire catalyst layer, a heat exchange type reactor, and a reaction method using the reaction tube.

Solutions to the Problems

The inventor of the present invention found that an essential cause of the above-mentioned problems in the fixed-bed flow reaction using a multitubular heat exchange type reactor is that the reaction ratio inevitably increases in the vicinity of the reaction tube inlet, which is a reaction region with high reaction raw material concentration. The inventor found that the problems can be solved by forming a volume gradient in which the catalyst amount gradually increases from the inlet part to the outlet part of reaction tubes, and this finding led to completion of the present invention.

Hereinafter, the present invention will be described.

[1] A packing for a reaction tube, wherein the volume is continuously or step-by-step decreased from one end part or midway toward the other end part.

[2] The packing for a reaction tube according to the above [1], further having an opening part to allow passage of fluids.

[3] The packing for a reaction tube according to the above [2], wherein a ratio of the opening part decreases from one end part with a large volume to the other end part with a small volume.

[4] The packing for a reaction tube according to any one of the above [1] to [3], wherein the figure is a pyramid, a truncated pyramid, a half ellipsoid, or a half spindle.

[5] The packing for a reaction tube according to the above [4], wherein the figure is a cone.

[6] The packing for a reaction tube according to any one of the above [1] to [5], comprising a plurality of circular tubes having different tube diameters, wherein the circular tubes are concentrically arranged in a step-by-step decreasing order of tube diameters from an outer periphery part to a center part, and the packing for a reaction tube has an opening part on a boundary part between steps.

[7] A reaction tube, comprising a structure therein, wherein the volume of the structure is continuously or step-by-step decreased from one end part or midway toward the other end part.

[8] The reaction tube according to the above [7], wherein the structure further has an opening part to allow passage of fluids.

[9] The reaction tube according to the above [8], wherein a ratio of the opening part decreases from one end part of the structure with a large volume to the other end part of the structure with a small volume.

[10] The reaction tube according to any one of the above [7] to [9], wherein the maximum cross-sectional area of the structure is 10% or more and 100% or less of the cross-section area of the reaction tube, the minimum cross-sectional area of the structure is 0% or more and 50% or less of the cross-section area of the reaction tube, and the length of the structure is 10% or more and 90% or less of the length of a catalyst layer.

[11] The reaction tube according to any one of the above [7] to [10], wherein the figure of the structure is a pyramid, a truncated pyramid, a half ellipsoid, or a half spindle.

[12] The reaction tube according to the above [11], wherein the figure of the structure is a cone.

[13] The reaction tube according to any one of the above [7] to [12], wherein the structure comprises a plurality of circular tubes having different tube diameters, the circular tubes are concentrically arranged in a step-by-step decreasing order of tube diameters from an outer periphery part to a center part, and the structure has an opening part on a boundary part between steps

[14] A heat exchange type reactor, comprising the reaction tube according to any one of the above [7] to [13].

[15] A reaction method comprising the step of getting a raw material fluid through the reaction tube according to any one of the above [7] to [13] filled with a catalyst from the end part side with a large volume of the structure.

Effect of the Invention

The present invention solves various problems attributed to the load unevenly placed on the catalyst in the vicinity of the reaction tube inlet, which has been inevitable in conventional multitubular reactors. More specifically, the present invention has effects of improving capability of heat removal or heat supply, suppressing local deterioration of a catalyst, improving the selectivity or conversion, improving the workability of catalyst replacement, and reducing the pressure loss of a catalyst layer.

BRIEF DESCRIPTION OF THE DRAWINGS

FIG. 1 is a cross-sectional view of a conical packing for a reaction tube, which is one embodiment of the packing for a reaction tube of the present invention.

FIG. 2 is a cross-sectional view of a packing for a reaction tube having a shape formed by concentrically arranging circular tubes in order of decreasing the tube diameter step-by-step from the outer periphery part to the center part, which is one embodiment of the packing for a reaction tube of the present invention.

FIG. 3 is a perspective view of a packing for a reaction tube having a shape formed by concentrically arranging circular tubes in order of decreasing the tube diameter step-by-step from the outer periphery part to the center part, which is one embodiment of the packing for a reaction tube of the present invention.

FIG. 4 is a schematic view for describing the shape formed by concentrically arranging circular tubes in order of decreasing the tube diameter step-by-step from the outer periphery part to the center part.

FIG. 5 is a schematic view for describing a method for rolling a right-angled triangular or right-angled trapezoidal metal thin sheet into a cone to produce a structure having a gap between turns of the metal thin sheet.

FIG. 6 is an illustration showing a reaction tube of an upward flow type reactor in which the structure of the present invention is placed and which is filled with a catalyst.

FIG. 7 is an illustration showing one embodiment of a reaction tube in which the structure of the present invention is placed and which is filled with a catalyst.

FIG. 8 is a graph showing the temperature distribution of catalyst layers in Example 1 and Comparative Example 1.

FIG. 9 is a graph showing the temperature distribution of catalyst layers in Example 2 and Comparative Example 2.

FIG. 10 is a graph showing the temperature distribution of catalyst layers in Example 3 and Comparative Example 3.

FIG. 11 is a cross-sectional view of a part in which a structure is placed in the reaction tubes used in Example 4 and Comparative Example 4.

FIG. 12 is a graph showing the temperature distribution of catalyst layers in Example 4 and Comparative Example 4.

FIG. 13 is a graph showing the temperature distribution of the catalyst layer in Example 5.

MODE FOR CARRYING OUT THE INVENTION

Hereinafter, the present invention will be described further in detail.

A packing for a reaction tube of the present invention (hereinafter, sometimes simply referred to as "packing") has a shape in which the volume is decreased from one end part in the inlet side of a reaction tube into which a raw material fluid is introduced or from the midway toward the other end part, and the packing is placed in the reaction tube in a manner that the packing volume gradually decreases from the reaction tube inlet side to the outlet side. Accordingly, the reaction tube volume can have a volume gradient that the volume gradually increases from the vicinity of the reaction tube inlet part toward the outlet part, and the amount of the catalyst filled into the reaction tube can be gradually increased from the vicinity of the reaction tube inlet part toward the outlet part. Further, the packing for a reaction tube has a structure through which fluids of a reaction raw material can pass, for example, pores or meshes, to effectively distribute and supply the fluid to the catalyst present in the periphery of the packing for a reaction tube.

The packing for a reaction tube of the present invention has a portion which can be called as a bottom face part. Such a bottom face part is an end part having the widest cross-sectional area in the direction at right angle to the height direction of the packing. For example, in the case where the packing has an upper face part in addition to side face parts, the bottom face part has a larger area than the upper face part. Placing the packing in a reaction tube in a manner that the bottom face part is near the inlet side of the raw material fluid in the catalyst layer in the reaction tube allows reduction of the catalyst amount near the inlet side of the raw material fluid in the catalyst layer in the reaction tube in accordance with the area of the bottom face part, and enables suppression of generation of a local abnormally-high temperature part or a local abnormally-low temperature part in the catalyst layer inlet side. Such a bottom face part does not have to be a complete plane, and may be uneven or may have holes or meshes to an extent that no catalyst penetrates the inside. Further, in the case where the bottom face part has a contact with a perforated plate in the reaction tube to prevent penetration of a catalyst in the packing, the state that nothing exists in the bottom face part of the packing is allowed.

The packing for a reaction tube of the present invention is characterized by having a shape in which the volume is continuously or step-by-step decreased from one end part or midway toward the other end part.

The "end part" corresponds to the above-mentioned bottom face part and means an end part having the widest cross-sectional area in the direction at right angle to the height direction of the packing. The "height direction of the packing" herein means the longest direction from one end part of the packing to the other end part on the opposite side.

The "midway" means a point between the bottom face part and the other end part. The other end part is an end part on the opposite side to the bottom face part and may be, for example, an upper face part in the case where the packing has the upper face part and an apex in the case where the packing is a cone. The position of such "midway" from the bottom face part in the height direction of the packing is not more than 70%, preferably not more than 60% or not more than 50%, more preferably not more than 40%, not more than 30%, or not more than 20%, and particularly preferably not more than 15% or not more than 10% in the case where the position of the bottom face part is regarded as 0% and the position of the other end part is regarded as 100% in the height direction of the packing.

In the present invention, the "shape in which the volume is continuously decreased" means a shape in which the cross-sectional area in the direction at right angle to the height direction of the packing becomes smaller as the distance from the bottom face part of the packing is longer. Further, the "shape in which the volume is step-by-step decreased" means a shape in which the area of the other end part of the packing is small as compared with the area of the bottom face part, and there exists one or more points having a cross-sectional area in the direction at right angle to the height direction of the packing same as a cross-sectional area at a position at a different distance from the bottom face part, and the cross-sectional area at a position at a longer distance from the bottom face part is not more than that at a position at a shorter distance therefrom. That is, the "volume" corresponds to the cross-sectional area in the direction at right angle to the height direction of the packing.

When being placed in the reaction tube, the packing for a reaction tube of the present invention may have any outer shape as long as the shape is one in which the volume is decreased from the end part at the side where a raw material fluid is introduced or from the midway toward the other end part, and the volume change may be continuous or step-by-step. The shape is preferably a pyramid, a truncated pyramid, a half ellipsoid, or a half spindle that is easy to be formed, and particularly preferably a cone or a truncated cone. Such a shape allows the packing together with a solid catalyst to fill reaction tubes of a conventional multitubular heat exchange type reactor in a catalyst-filled state in which the catalyst amount continuously or step-by-step increases from the reaction tube inlet side to the outlet side. Therefore, a reaction in the vicinity of the inlet of the reaction tube, where the reaction raw material concentration is high and the reaction ratio is high, can be made to proceed moderately.

In the present invention, the "pyramid" is a three-dimensional object formed by connecting all points of a closed curve such as a circle or a polygon on a plane to one point outside of the plane. The "truncated pyramid" is a solid figure formed by removing a similar reduced pyramid having an apex in common with the original pyramid from the original pyramid. The "cone" and "truncated cone" mean a "pyramid" and a "truncated pyramid" with a circular bottom shape, respectively. The "ellipsoid" is expressed by an equation of $x^2/a^2+y^2/b^2+z^2/c^2=1$ (in the equation, a, b, and c represent a half length of the diameter in the x-axis, y-axis, and z-axis directions, respectively), and is a three-dimensional object surrounded with ellipsoidal faces. In the present invention, the "half ellipsoid" is a shape formed by cutting an ellipsoid along a cross section including the center in the direction at right angle to the longest direction among the x-axis, y-axis, and z-axis directions. The "spindle" has a cylindrical shape with a thickest center part and gradually tapered both ends. The spindle is similar to an ellipsoid in shape, but cannot be represented by the above-mentioned equation. In the present invention, the "half spindle" has a shape formed by cutting a spindle along a cross section including the center in the direction at right angle to the longest direction among the x-axis, y-axis, and z-axis directions.

Strictly, the case where the cross-sectional area decreases step-by-step from the bottom face part toward the other end part or the case where the cross-sectional area decreases from midway between the bottom face part and the other end part are not included in the above mention "pyramid." However, in the present invention, these shapes are included in the "pyramid" as long as the rough outline can be regarded as a pyramid.

FIG. 1 shows a cross-sectional view of a conical packing for a reaction tube. FIG. 2 and FIG. 3 respectively show a cross-sectional view and a perspective view of the packing for a reaction tube having a shape formed by concentrically arranging a plurality of circular tubes having different diameters in order of decreasing the tube diameter step-by-step from the outer periphery part to the center part. As shown in these examples, the packing of the present invention has a bottom face part, and has a shape having a cross-sectional area continuously or step-by-step decreased from the bottom face part toward the other end part or from midway between the bottom face part and the other end part toward the other end part in the direction at right angle to the height direction. Meanwhile, the present invention is not limited to the embodiments shown in the drawings.

A material of the packing for a reaction tube is not particularly limited as long as it has heat resistance at the reaction temperature, and metals and ceramics may be used.

The size of the packing of the present invention may be determined properly in accordance with the size of reaction tubes to be used and the type of reaction. In general, for example, the bottom face part may have a circle equivalent diameter around not less than 5 mm and not more than 40 mm and a height around not less than 20 mm and not more than 10 m.

More specifically, the size of the packing may be determined properly in accordance with the catalyst layer in a reaction tube in which the packing is to be inserted. For example, the ratio of the maximum cross-sectional area of the packing, that is, the area of the bottom face part of the packing to the inner cross-sectional area of the reaction tube, that is, the cross-sectional area of the catalyst layer is preferably not less than 10%, and more preferably not less than 30%. A ratio not less than 10% can more reliably reduce the load on the catalyst in the inlet part of the reaction tube, that is, the introduction side of raw material fluid of the catalyst layer. The ratio is preferably not more than 100%, and more preferably not more than 60%. As described later, even if the ratio is 100%, providing an opening part in the bottom face part of the packing makes introduction of the raw material fluid into the catalyst layer possible.

The ratio of the minimum cross-sectional area of the packing, that is, the cross-sectional area of the end part opposite to the bottom face part of the packing to the inner cross-sectional area of the reaction tube, that is, the cross-sectional area of the catalyst layer is preferably not less than 0% and not more than 50%, and more preferably not more than 30%. The ratio of 0% means that the cross-sectional area of the end part opposite to the bottom face part of the packing is zero, and the shape of the packing is a pyramid. A ratio of 50% or less can more reliably suppress decrease of the reaction efficiency.

The height of the packing is preferably not less than 10%, and more preferably not less than 20% of the length of the catalyst layer in the reaction tube. A ratio not less than 10% can more reliably reduce the load on the catalyst in the inlet part of the reaction tube, that is, the introduction side of raw material fluid of the catalyst layer. On the other hand, the ratio is preferably not more than 90%, and more preferably not more than 60%. A ratio of 90% or less can more reliably suppress decrease of the reaction efficiency.

The packing for a reaction tube of the present invention preferably has an opening part, through which a raw material fluid can pass in the direction from the inside to the outer surface. Providing an opening part in the structure of the packing to allow the raw material fluid to pass therethrough enables the raw material fluid to contact with the catalyst dispersively in the periphery of the packing, and therefore further reduced the evenness of the reaction ratio. In this case, the packing has an effect of improving the porosity of the catalyst layer and can lower the pressure loss of the catalyst layer.

The shape of the opening part in the packing is not particularly limited, and may be any shape as long as the raw material fluid can flow in the inside of the packing from the outside and flow out again to the outside. For example, the shape may be holes with a diameter about not less than 50 µm and not more than 2 mm, and the packing may have a net structure having a mesh opening dimension of not less than 20 µm and not more than 2 mm. The diameter is more preferably not less than 100 µm, furthermore preferably not less than 200 µm, and more preferably not more than 1.5 mm, furthermore preferably not more than 1 mm. The mesh opening dimension is more preferably not less than 35 µm, furthermore preferably not less than 70 µm or not less than 150 µm, and more preferably not more than 900 µm or not more than 500 µm, furthermore preferably not more than 300 µm.

The opening ratio of the packing for a reaction tube of the present invention is not particularly limited, and may be 20 to 85% of the surface area of the packing. Particularly, an opening ratio of 30 to 85% is preferable in terms of decrease of the pressure loss. The opening diameter may be selected properly to give the above-mentioned opening ratio.

The opening ratio is preferably decreased from the end part having a larger volume of the packing toward the other end part having a smaller volume of the packing, that is, from the bottom face part toward the other end part. Such an embodiment makes the degree of dispersion of the raw material fluid in the catalyst layer in the reaction tube more uniform.

Additionally, the opening part may have an opening ratio decreased from the end part in the reaction tube inlet side, that is, the bottom face part toward the other end part, and accordingly, the flow amount of the raw material fluid can be controlled from the reaction tube inlet part to the outlet part. As a result, the degree of dispersion of the raw material fluid in the catalyst layer in the reaction tube can be made more uniform. For example, provided that the position of the bottom face part is regarded as 0% and the position of the other end part is regarded as 100% in the height direction of the packing, the opening ratio to the surface area in the range from not less than 0% to not more than 35% in the height direction can be made not less than 40% and not more than 70%; the opening ratio to the surface area in the range from more than 35% to not more than 70% in the height direction can be made not less than 30% and not more than 40%; and the opening ratio to the surface area in the range from more than 70% to not more than 100% in the height direction can be made not less than 10% and not more than 30%. In the present invention, the "opening ratio" is defined as the percentage of the area of openings in the side face part and bottom face part of the packing of the present invention or a portion thereof.

In the case where the packing has a structure having an opening part through which the raw material fluid can pass in the direction from the inside to the outer surface, for example, a high pressure loss between the inlet and the outlet of the reaction tube may possibly increase the amount of the raw material fluid passing through the inner space of the packing more than necessary. In such a case, the passing amount of the raw material fluid through the inner space of the packing can be adjusted by filling the inside of the packing with an inactive solid (e.g., metal spheres and ceramic balls) and thereby generating ventilation resistance.

The packing for a reaction tube having a shape in which the volume is decreased step-by-step from an end part or from midway toward the other end part may have a shape formed by concentrically arranging a plurality of circular tubes having different tube diameters in a step-by-step decreasing order of tube diameters from an outer periphery part to a center part.

Such a shape may be shown in, for example, FIG. 4. FIG. 4 is a schematic view for describing the shape, and does not show any method for producing the above-mentioned packing for a reaction tube.

The diameter of the tubes in each step for producing the above-mentioned packing for a reaction tube may be determined properly in accordance with the reaction tube diameter, the catalyst size, the catalyst activity, and the reaction conditions. Further, the length of the tubes in each step, for example, $h_1$ to $h_5$ in FIG. 3, may be adjusted properly in accordance with the catalyst layer length of the reaction tubes, the catalyst activity, and the reaction conditions. The tube length in each step may be the same or different, and, for example, the tube length may be decreased or increased step-by-step with the step-by-step decrease of the tube diameter. The outer shape with step-by-step decrease of the tube length with the step-by-step decrease of the tube diameter is more preferable.

The number of steps of the packing for a reaction tube is generally not less than 2 and not more than 10, and preferably not less than 3 and not more than 5.

The packing for a reaction tube preferably has the opening part at least on the boundary parts between steps. The boundary parts mean, as shown in FIG. 3, portions parallel or approximately parallel to the bottom face part between neighboring steps. Providing the opening parts in the portions enables more precise control of the flow amount of the raw material fluid.

In the case of providing the opening parts on the boundary parts between steps, the packing can be produced from a plurality of circular tubes having different diameters by, for example, inserting a smaller diameter tube into the inside of a larger diameter tube with the center axes thereof aligned with each other and concentrically arranging the tubes. In this case, the diameter decreases step-by-step from the outer periphery part to the center part, and a gap is formed between the outer wall of the circular tube disposed in the inner side and the inner wall of the circular tube disposed adjacently in the outer side to give a structure having the opening part. The wall thickness of the tubes composing circular tubes is generally not less than 0.05 mm and not more than 0.3 mm.

It is also allowed to use a packing for a reaction tube having a structure formed by rolling a right-angled triangular or right-angled trapezoidal metal thin sheet into a cone to produce a gap between turns of the metal thin sheet. The right-angled trapezoid means a trapezoid of which 2 interior angles among 4 interior angles are 90°.

Such a packing for a reaction tube can be produced as shown in, for example, FIG. 5. That is, a conical shape can be formed by rolling the metal sheet in a manner that the interior angle of 90° of a right-angled triangle or 2 interior angles of 90° of a right-angled trapezoid are set in the lower side and the longer sides are set in the inner side. In this case, a gap is formed between turns of the metal sheet, and the gap serves as an opening part through which fluids pass from the bottom face part side.

The thickness of the metal thin sheet for forming the packing for a reaction tube is not particularly limited, and may be, for example, not less than 0.05 mm and not more than 0.3 mm. The length of the base of the right-angled triangle shown in FIG. 5 and the length of the side having 90° of both ends angle of the right-angled trapezoid may be not less than 3 times and not more than 15 times as long as the reaction tube diameter.

In the case of a packing having a closed structure without opening part through which the raw material fluid can pass, a convex part having a function of dispersing the raw material fluid may be provided in the bottom face side. For example, the entire bottom face part may be formed into a half sphere or a half ellipsoid.

In the case where a reactor is of a downward flow type, the packing for a reaction tube can be placed in the inside of the reaction tube without problem by covering the end of the packing with a detachable convex cover in the reactor inlet side, and filling the gap between the packing and the reaction tube with a catalyst.

The reaction tube of the present invention may be one usable particularly as a reaction tube of a multitubular heat exchange type reactor, and is characterized by having a catalyst layer which internally includes a structure having a shape in which the volume is continuously or step-by-step decreased from one end part or from midway toward the other end part; that is, a structure having a bottom face part and having a shape in which the cross-sectional area is continuously or step-by-step decreased from the bottom face part toward the other end part, or from the midway between the bottom face part and the other end part toward the other end part in the direction at right angle to the height direction.

The structure included in the inside of the reaction tube of the present invention is not particularly limited as long as the structure has the above-mentioned shape. For example, the packing may be the above-mentioned packing for a reaction tube filled together with the catalyst, or the structure may correspond to the above-mentioned packing for a reaction tube fixed in the reaction tube before the reaction tube is filled with the catalyst. In the above-mentioned definition or description of the packing, the "packing" may be interpreted as the "structure." The reaction tube in which the structure is fixed allows physical distribution therethrough even in a state where it is not filled with the catalyst.

The shape and the size of the reaction tube may be determined properly in accordance with the type and the execution scale of the reaction. For example, the inner diameter may be adjusted to be around not less than 20 mm and not more than 50 mm, and the height may be adjusted to be around not less than 0.1 m and not more than 20 m. The outer diameter and the inner diameter of the reaction tube do not have to be uniform, but are preferably uniform since the production cost is increased if the outer diameter and the inner diameter are not uniform. The shape of the reaction tube may be straight as shown in FIG. 6, or may be U-shaped as shown in FIG. 7.

The size of the structure to be placed in the inside of the reaction tube may be determined properly in accordance with the size of the reaction tube to be used and the type of reaction. For example, the ratio of the maximum cross-sectional area of the structure, that is, the area of the bottom face part of the structure to the cross-sectional area of the reaction tube is preferably not less than 10% and not more than 100%, and more preferably not less than 30% and not more than 60%. If the ratio is not less than 10%, a local abnormally-high temperature part and a local abnormally-low temperature part in the vicinity of the inlet of the reaction tube can be more reliably suppressed. Even in the case where the ratio is 100%, providing an opening in the bottom face part of the structure allows flow of the raw material fluid. Further, the ratio of the minimum cross-sectional area of the structure to the cross-sectional area of the reaction tube is preferably not less than 0% and not more than 50%, and more preferably not less than 0% and not more than 30%. The reaction proceeds well if the ratio is in that range. Further, the ratio of the length (height) of the structure to the length of the catalyst layer in the reaction tube is preferably not less than 10% and not more than 90%, and more preferably not less than 20% and not more than 60%. If the ratio is not less than 10%, a local abnormally-high temperature part and a local abnormally-low temperature part in the vicinity of the inlet of the reaction tube can be more reliably suppressed. The reaction proceeds well if the ratio is not more than 90%. In addition, in the case of the above-mentioned reaction tube including the structure fixed therein and not filled with any catalyst, the length (height) of the structure may be determined on the basis of the length of the catalyst layer to be filled therein.

The structure may have a hole for leading a protection tube for protecting a thermometer as shown in FIG. 7.

In the case of placing the packing for a reaction tube as the above-mentioned structure in the reaction tube, the packing for a reaction tube is inserted in the inside of the reaction tube from the reaction tube inlet part or the outlet part. The position of placing the above-mentioned structure in the axial direction is adjusted in a manner that the reaction tube inlet end is aligned with the bottom face part of the structure, and the position of placing the structure in the diameter direction is adjusted in a manner that the center axis of the reaction tube is aligned with the center axis of the structure. However, if these positions are slightly shifted, the effect may be caused without any problem. The above-mentioned reaction tube inlet part may be the end part in the introduction side of the raw material fluid in the catalyst layer in the reaction tube.

FIG. 6 is a cross-sectional view of a reaction tube of an upward flow type reactor filled with the catalyst after the packing shown in FIG. 1 is placed therein. The ratio of the circle equivalent radius (r) of the bottom face part of the structure to the reaction tube inner radius (R) in FIG. 6 is in a range of $(r/R)^2=0.1$ to 1.0, and the ratio of the height (h) of the structure to the catalyst layer height (H) is in a range of $h/H=0.1$ to $0.9$. These ratios may be selected to be their optimum values in accordance with the catalyst activity, selectivity, the size of the catalyst, the pressure loss between the inlet and outlet of the reaction tube, and the reaction conditions.

The reactor of the present invention is filled with the catalyst by a common method, that is, a method of pouring the catalyst from the upper part of the reaction tube. In a multitubular heat exchange type reactor including reaction tubes in which the structure of the present invention is placed, a prescribed amount of a catalyst has only to be poured from the upper part of each reaction tube. Since the similar filling speed and the similar catalyst layer height make the pressure loss even, it is unnecessary to finely adjust the pressure loss by additional filling a material for pressure loss adjustment.

The heat exchange type reactor of the present invention has the above-mentioned reaction tube. The number of reaction tubes is not particularly limited, and may be 1 or more. In the case of industrially producing an desired compound, the reactor generally has not less than a thousand and not more than thirty thousands of the reaction tubes.

The heat exchange type reactor of the present invention includes a reaction tube including the structure of the present invention and having a catalyst layer filled with a catalyst. A heat medium is circulated around the reaction tube to supply heat needed for the reaction to the catalyst layer or to absorb excess reaction heat.

The present invention also relates to a reaction method using the reaction tube in which the structure is placed and which is filled with a catalyst. More particularly, the reaction method of the present invention includes a step of flowing a raw material fluid through the reaction tube of the present invention from an end part side with a larger volume of the structure, that is, the bottom face part side. In this case, the structure of the present invention reduces the dense contact of the raw material fluid with the catalyst in the vicinity of the inlet side of the catalyst layer in the reaction tube where a local abnormally-high temperature part or a local abnormally-low temperature part tends to be generated, and gradually increases the frequency of the contact along the flow direction of the raw material fluid. As a result, generation of a local abnormally-high temperature part or a local abnormally-low temperature part in the vicinity of the reaction tube inlet can be suppressed to extend the catalyst life and prevent reduction of the reaction efficiency.

The reaction using the reaction tube in which the structure of the present invention is placed and which is filled with a catalyst is not particularly limited, and may include an exothermic reaction and an endothermic reaction. The reaction is preferably a vapor-phase oxidation or a vapor-phase reduction, and may include, for example, a vapor-phase oxidation that emits large amount of heat, such as maleic anhydride production by oxidation of benzene, ethylene oxide production by oxidation of ethylene, acrolein and acrylic acid production by oxidation of propylene, acrylic acid production by oxidation of acrolein, methacrolein and methacrylic acid production by oxidation of isobutylene, and methacrylic acid production by oxidation of methacrolein, and a vapor-phase dehydration that absorbs large amount of heat, such as ethyleneimine production by dehydration of monoethanolamine, and N-vinyl-2-pyrrolidone production by dehydration of N-(2-hydroxyethyl)-2-pyrrolidone.

The catalyst to be filled in the reaction tube in which the structure of the present invention is placed is not particularly limited, and known catalysts which have conventionally been used in the above-mentioned reactions may be used.

The shape of the catalyst is also not particularly limited, and spherical, columnar, and ring-shaped catalysts can be used.

The vapor-phase catalytic reaction using the reaction tube in which the structure of the present invention is placed can be carried out in the conditions same as before. For example, a propylene oxidation may be carried out by passing a gas mixture containing 1 to 12 volume % of propylene, 2 to 20 volume % of molecular oxygen, 0 to 50 volume % of water vapor, and the balance of an inert gas such as nitrogen and carbon dioxide as well as propane at a heat medium temperature of 280 to 450° C., a space velocity (GHSV) of 300 to 5000 h$^{-1}$ and a reaction pressure of 0.1 to 1.0 MPa through the catalyst layer.

An acrolein oxidation may be carried out by passing a gas mixture containing 1 to 12 volume % of acrolein, 2 to 20 volume % of molecular oxygen, 0 to 25 volume % of water vapor, and the balance of an inert gas such as nitrogen and carbon dioxide at a heat medium temperature of 200 to 400° C., a space velocity (GHSV) of 300 to 5000 h$^{-1}$ and a reaction pressure of 0.1 to 1.0 MPa through the catalyst layer.

A benzene oxidation may be carried out by passing a gas mixture containing 1 to 2 volume % of benzene, 10 to 30 volume % of molecular oxygen, 0 to 6 volume % of water vapor, and the balance of an inert gas such as nitrogen and carbon dioxide at a heat medium temperature of 340 to 380° C., a space velocity (GHSV) of 1900 to 4000 h$^{-1}$ and a reaction pressure of 0.1 to 1.0 MPa through the catalyst layer.

An intramolecular dehydration of monoethanolamine as an example of the endothermic reaction may be carried out by passing 100% monoethanolamine gas at a heat medium temperature of 300 to 450° C., a space velocity (GHSV) of 10 to 300 h$^{-1}$ and a reaction pressure of 5 to 30 kPa through the catalyst layer.

The reaction starting operation is conventionally generally carried out by a method for gradually increasing the reaction raw material gas concentration over a long time to suppress the local temperature increase or local temperature decrease at the reactor inlet part, whereas the reaction using the reaction tube in which the structure of the present invention is placed can achieve a prescribed raw material concentration within a time remarkably shortened compared to the conventional reaction.

This application claims the benefit of priority to Japanese Patent Application No. 2013-231370 filed on Nov. 7, 2013. The disclosure of Japanese Patent Application No. 2013-231370, filed on Nov. 7, 2013, is incorporated by reference herein in its entirety.

EXAMPLES

Hereinafter, the present invention will be described in detail with reference to examples and comparative examples, but the present invention is not limited to these examples.

The conversion, selectivity, one pass yield, and space velocity in the present invention are defined as follows.

Conversion(mol %)=(number of moles of reacted reaction raw material)/(number of moles of supplied reaction raw material)×100

Selectivity(mol %)=(number of moles of produced desired product)/(number of moles of reacted reaction raw material)×100

One pass yield (mol %)=(number of moles of produced desired product)/(number of moles of supplied reaction raw material)×100

Space velocity (NL/L·hr)=supply amount of reaction raw material per hour (NL/hr: conversion in standard state)/filled catalyst amount (L)

Example 1

(1) Packing for Reaction Tube

A truncated conical packing made of a stainless steel net having a mesh opening dimension of 250 μm and having a bottom face diameter of 10 mm, an upper face diameter of 4 mm, and a height of 65 mm was used. A hole (having a diameter of about 3.1 mm) for leading a tube (having an inner diameter of 2 mm, an outer diameter of 3 mm, and a length of 320 mm) for placing a thermocouple for measuring the temperature during of reaction was formed on the apex part.

(2) Placing Packing for Reaction Tube in Reaction Tube and Oxidation of Benzene

A U-shaped tube of stainless steel having an inner diameter of 25 mm and having a side tube at both ends for flowing a gas in and out was used as a reaction tube. The packing for a reaction tube was placed in a position in a manner that the bottom face thereof could have contact with a perforated plate for supporting a catalyst included in a thermocouple-setting tube (having an inner diameter of 2 mm, an outer diameter of 3 mm, and a length of 320 mm). The packing was placed in the inside of the reaction tube by inserting the packing from the catalyst charging hole of the reaction tube to the bottom end. Next, 80 mL of a ring shaped catalyst having an outer diameter of 6 mm, an inner diameter of 2 mm, and a height of 6 mm and containing vanadium, molybdenum, and phosphorus as main components was filled as a catalyst for oxidation of benzene. The inside of the reaction tube filled with the packing for a reaction tube and the catalyst is shown in FIG. 7. The reaction tube in this state was immersed in a molten salt bath of 360° C.

A gas mixture containing 1.6 volume % of benzene, 21 volume % of oxygen, 5 volume % of water vapor, and the balance of an inert gas was supplied at a space velocity of 2500/h from the bottom part (inlet part) of the catalyst layer toward the upper part (outlet part) to oxidize benzene. The conversion 1 hour after starting of gas supply was 84.6%, the selectivity of maleic anhydride was 83.0%, the one pass yield was 70.2%, and the highest temperature of the catalyst layer was 420° C. The temperature of the catalyst layer was distributed as shown in FIG. 8.

Comparative Example 1

Oxidation of benzene was carried out in the same manner as described in Example 1, except that a packing for a reaction tube described above was not used. The conversion 1 hour after starting of gas supply was 81.6%, the selectivity of maleic anhydride was 81.0%, the one pass yield was 66.1%, and the highest temperature of the catalyst layer was 430° C. The temperature of the catalyst layer was distributed as shown in FIG. 8.

From the results shown in FIG. 8, use of the reaction tube in which the packing of the present invention was placed lowered the catalyst layer temperature in the vicinity of the reaction tube inlet. From the results, decrease of the reaction load on the catalyst in the vicinity of the reaction tube inlet is made clear. Further, elimination of unevenness of the reaction was proved to contribute to significant improvement of the conversion and selectivity.

Example 2

A reaction tube containing the same packing for a reaction tube as shown in Example 1 and having the same size as shown in Example 1 was filled with 50 mL of a ring catalyst having an outer diameter of 6 mm, an inner diameter of 2 mm, and a height of 6 mm and containing molybdenum and bismuth as main components as a catalyst for oxidation of propylene, and thereafter immersed in a molten salt bath of 320° C. A gas mixture containing 2 volume % of propylene, 12 volume % of oxygen, 40 volume % of water vapor, and the balance of an inert gas was supplied at a space velocity of 1350/h from the bottom part (inlet part) of the catalyst layer toward the upper part (outlet part) to oxidize propylene. The highest temperature of the catalyst layer was 347° C. and the temperature of the catalyst layer was distributed as shown in FIG. 9.

Comparative Example 2

Oxidation of propylene was carried out in the same manner as described in Example 2, except that packing for a reaction tube described above was not used. The highest temperature of the catalyst layer was 351° C. and the temperature of the catalyst layer was distributed as shown in FIG. 9.

From the results shown in FIG. 9, when a reaction tube equipped with the packing of the present invention was not used (Comparative Example 2), the temperature of the catalyst layer was highest in the vicinity of the raw material introduction part, and decreased gradually toward the travelling direction of the raw material. On the other hand, use of the reaction tube in which the packing of the present invention was placed (Example 2) lowered the highest temperature of the catalyst layer from 351° C. to 347° C., and further reduced the temperature change in the catalyst layer.

Example 3

A reaction tube containing the same packing for a reaction tube as shown in Example 1 and having the same size as shown in Example 1 was filled with 50 mL of a spherical catalyst having a diameter of 5.5 mm and containing molybdenum and vanadium as main components as a catalyst for oxidation of acrolein, and thereafter immersed in a molten salt bath of 230° C.

A gas mixture containing 2 volume % of acrolein, 10 volume % of oxygen, 10 volume % of water vapor, and the balance of nitrogen was supplied at a space velocity of 2000/h from the bottom part (inlet part) of the catalyst layer toward the upper part (outlet part) to oxidize acrolein. The highest temperature of the catalyst layer was 253° C. and the temperature of the catalyst layer was distributed as shown in FIG. 10.

Comparative Example 3

Oxidation of acrolein was carried out in the same manner as described in Example 3, except that a packing for a reaction tube was not used. The highest temperature of the catalyst layer was 262° C. and the temperature of the catalyst layer was distributed as shown in FIG. 10.

Similarly to that in Example 2, the temperature of the catalyst layer in the vicinity of the reaction tube inlet and the highest temperature of the catalyst layer were lowered also in Example 3, and placing the packing of the present invention was proved to contribute to reduction of the reaction load on the entire catalyst layer, particularly on the catalyst in the vicinity of the reaction tube inlet.

Example 4

(1) Reaction Tube

A stainless steel pipe having an inner diameter of 25 mm installed with a packing produced by concentrically arranging three stainless steel pipes having different tube diameters and tube lengths (outer diameter 10 mm, inner diameter 9.4 mm, and length 60 mm; outer diameter 8 mm, inner diameter 7.4 mm, and length 90 mm; and outer diameter 6 mm, inner diameter 5.4 mm, and length 110 mm) in its inner end part was used as a reaction tube. A protection tube (having an inner diameter of 2 mm, an outer diameter of 3 mm, and a length of 320 mm) for a thermocouple for measuring the temperature during the reaction was inserted in the center part of the structure. FIG. 11 is a cross-sectional view of the portion of the reaction tube in which the structure is to be placed.

(2) Oxidation of Propylene

This reaction tube was filled with 50 mL of the catalyst same as described in Example 1 and thereafter, the reaction tube was heated to 290° C. Next, a gas mixture containing 2 volume % of propylene, 12 volume % of oxygen, 40 volume % of water vapor, and the balance of an inert gas was supplied at a space velocity of 2700/h from the bottom part (inlet part) of the catalyst layer toward the upper part (outlet part) to oxidize propylene. The highest temperature of the catalyst layer was 310° C. and the temperature of the catalyst layer was distributed as shown in FIG. 12.

Comparative Example 4

Oxidation of propylene was carried out in the same manner as described in Example 4, except that a reaction tube without the structure of the present invention was placed was used and the temperature was controlled to be 280° C. The highest temperature of the catalyst layer was 316° C. and the temperature of the catalyst layer was distributed as shown in FIG. 12.

From the results shown in FIG. 12, when a reaction tube without the packing of the present invention was used (Comparative Example 4), the temperature of the catalyst layer was highest in the vicinity of the raw material introduction part, and decreased gradually toward the travelling direction of the raw material. On the other hand, use of the reaction tube in which the packing of the present invention was placed (Example 4) lowered the highest temperature of the catalyst layer from 316° C. to 310° C., and further reduced the temperature change in the catalyst layer.

Example 5

(1) Reaction Tube

A truncated conical structure having a bottom face diameter of 10 mm, an upper face diameter of 4 mm, and a height of 1800 mm was produced by rolling a right-angled triangular stainless steel net. The size of the stainless steel net was controlled to have a mesh opening dimension of 250 μm from the bottom face to 800 mm upper therefrom; a mesh opening dimension of 150 μm from 800 mm to 500 mm upper therefrom; and a mesh opening dimension of 75 μm further from 500 mm to the upper face. A reaction tube having an inner diameter of 25 mm and a length of 3000 mm, in which the structure was placed, was used for the reaction. A hole (having a diameter of about 3.1 mm) for leading a tube (having an inner diameter of 2 mm, an outer diameter of 3 mm, and a length of 3100 mm) for placing a thermocouple for measuring the temperature during the reaction was formed in the center of the structure.

(2) Production of Acrolein for Reaction Raw Material

A reaction tube filled with a catalyst for oxidation of propylene was immersed in a molten salt bath of 352° C., and a gas mixture containing 7 volume % of propylene, 12.6 volume % of oxygen, 7 volume % of water vapor, and the balance of an inert gas was supplied to the reaction tube at a space velocity of 1380/h to oxidize propylene. At that time, the propylene conversion was 98.0%, the one pass yield of acrolein was 80.4% and the one pass yield of acrylic acid was 12.5%.

(3) Oxidation of Acrolein

The reaction tube described in (1) was filled with 1286 mL of a spherical catalyst having a diameter of 5.2 mm and containing molybdenum and vanadium as main components as a catalyst for oxidation of acrolein. The molten salt bath temperature was controlled to be 265° C. and the gas produced in the process for producing the acrolein for reaction raw material described in (2) was supplied at a space velocity of 1544/h from the bottom part (inlet part) of the catalyst layer toward the upper part (outlet part) to oxidize acrolein. The acrolein conversion on the basis of the supplied acrolein amount was 99.8%, the selectivity of acrylic acid was 94.3%, and the one pass yield of acrylic acid was 94.1%. The highest temperature of the catalyst layer was 332° C. and the temperature of the catalyst layer was distributed as shown in FIG. 13.

Comparative Example 5

Oxidation of acrolein was carried out in the same manner as described in Example 5, except that no packing for a reaction tube was used. However, since the catalyst layer temperature was so sharply increased immediately after starting of the acrolein supply as to make temperature control impossible, the reaction was stopped.

INDUSTRIAL APPLICABILITY

Execution of an exothermic reaction or an endothermic reaction using a reaction tube in which a packing for a reaction tube of the present invention is placed and which is filled with a catalyst produce a compound at high productivity (high conversion, high selectivity, and long life), so that the industrial applicability of the packing for a reaction tube of the present invention in terms of economy is extremely high. Further, a risk of runaway reaction and explosion can be avoided, the packing for a reaction tube of the present invention makes significant contribution in terms of safety.

DESCRIPTION OF REFERENCE SIGNS

1. Reaction tube inlet part
2. Reaction tube outlet part
3. Catalyst
4. Reaction tube
5. Packing for reaction tube
6. Conical packing
7. Thermometer protection tube
8. Perforated plate
H. Catalyst layer length
h. Packing height
R. Reaction tube inner radius
r. Outer radius of bottom face of packing

The invention claimed is:

1. A packing for a reaction tube,
wherein the packing is to be placed near a reaction tube inlet side, and the packing together with a catalyst is to fill the reaction tube,
wherein
(i) a volume of the packing is continuously decreased from one end part at a side where a raw material fluid is introduced or midway toward another end part and the packing comprises an opening part to allow passage of fluids, or
(ii) a volume of the packing is step-by-step decreased from one end part at a side where a raw material fluid is introduced or midway toward another end part and the packing comprises an opening part to allow passage of fluids, the opening part being on a boundary part between steps, and
wherein a ratio of the opening part decreases from the one end part with a large volume to the other end part with a small volume.

2. The packing for a reaction tube according to claim 1, wherein a figure of the packing is a pyramid, a truncated pyramid, a half ellipsoid, or a half spindle.

3. The packing for a reaction tube according to claim 2, wherein the figure is a cone.

4. The packing for a reaction tube according to claim 1, wherein
the volume of the packing is step-by-step decreased, and
the packing further comprises a plurality of circular tubes having different tube diameters, wherein the circular tubes are concentrically arranged in a step-by-step decreasing order of tube diameters from an outer periphery part to a center part.

5. A reaction tube comprising a structure therein,
wherein
(i) a volume of the structure is continuously decreased from one end part in an inlet side of the reaction tube into which a raw material fluid is introduced or midway toward another end part in an outlet side of the reaction tube and the structure comprises an opening part to allow passage of fluids, or
(ii) a volume of the structure is step-by-step decreased from one end part in an inlet side of the reaction tube into which a raw material fluid is introduced or midway toward another end part in an outlet side of the reaction tube and the structure comprises an opening part to allow the passage of fluids, the opening part being on a boundary part between steps,
wherein the structure is near the inlet side of the reaction tube, wherein a catalyst is filled between the structure and the reaction tube, and wherein a ratio of the opening part decreases from the one end part of the structure with a large volume to the other end part of the structure with a small volume.

6. The reaction tube according to claim 5, wherein a maximum cross-sectional area of the structure is 10% or more and 100% or less of a cross-section area of the reaction tube, a minimum cross-sectional area of the structure is 0% or more and 50% or less of the cross-section area of the reaction tube, and a length of the structure is 10% or more and 90% or less of a length of a catalyst layer.

7. The reaction tube according to claim 5, wherein a figure of the structure is a pyramid, a truncated pyramid, a half ellipsoid, or a half spindle.

8. The reaction tube according to claim 7, wherein the figure of the structure is a cone.

9. The reaction tube according to claim 5, wherein
the volume of the structure is step-by-step decreased, and
the structure comprises a plurality of circular tubes having different tube diameters, the circular tubes being concentrically arranged in a step-by-step decreasing order of tube diameters from an outer periphery part to a center part.

10. A heat exchange type reactor, comprising the reaction tube according to claim 5.

11. The packing for a reaction tube according to claim 1, wherein
the volume of the packing is step-by-step decreased, and
the packing includes at least two steps having different volumes that are coaxial and free from overlap.

12. The reaction tube according to claim 5, wherein
the volume of the structure is step-by-step decreased, and
the structure includes at least two steps having different volumes that are coaxial and free from overlap.

* * * * *